(12) United States Patent
Rhim et al.

(10) Patent No.: US 8,881,592 B2
(45) Date of Patent: *Nov. 11, 2014

(54) ULTRASOUND PROBE

(75) Inventors: Sung Min Rhim, Incheon-si (KR); Ho Jung, Seoul (KR); Do Kyeong Kim, Siheung-si (KR)

(73) Assignee: Humanscan Co., Ltd., Ansan-Si, Gyeonggi-Do (KR)

( * ) Notice: Subject to any disclaimer, the term of this patent is extended or adjusted under 35 U.S.C. 154(b) by 259 days.

This patent is subject to a terminal disclaimer.

(21) Appl. No.: 13/521,997

(22) PCT Filed: Jul. 15, 2010

(86) PCT No.: PCT/KR2010/004601
§ 371 (c)(1),
(2), (4) Date: Jul. 12, 2012

(87) PCT Pub. No.: WO2011/087191
PCT Pub. Date: Jul. 21, 2011

(65) Prior Publication Data
US 2012/0285251 A1    Nov. 15, 2012

(30) Foreign Application Priority Data

Jan. 18, 2010 (KR) .................. 10-2010-0004542

(51) Int. Cl.
| | | |
|---|---|---|
| *G01N 29/00* | (2006.01) | |
| *G01N 29/24* | (2006.01) | |
| *A61N 7/02* | (2006.01) | |
| *B06B 1/06* | (2006.01) | |
| *A61N 7/00* | (2006.01) | |

(52) U.S. Cl.
CPC ............ *A61N 7/02* (2013.01); *B06B 1/0637* (2013.01); *A61N 2007/0065* (2013.01); *A61N 2007/0095* (2013.01); *A61N 2007/0078* (2013.01)
USPC ............................................ 73/632; 73/649

(58) Field of Classification Search
USPC .................................................. 73/632, 649
See application file for complete search history.

(56) References Cited

U.S. PATENT DOCUMENTS 5,123,418 A * 6/1992 Saurel et al. ................... 600/459
5,195,372 A * 3/1993 Fushimi et al. ................. 73/593

(Continued)

FOREIGN PATENT DOCUMENTS

EP     1274348       9/2007
JP     06261908      9/1994

(Continued)

OTHER PUBLICATIONS

International Search Report mailed Feb. 24, 2011 for PCT/KR2010/004601.
Japanese Office Action for application No. 2012-549916 dated Aug. 26, 2013.

(Continued)

*Primary Examiner* — J M Saint Surin
(74) *Attorney, Agent, or Firm* — Lowe Hauptman & Ham, LLP (57) ABSTRACT

The present invention relates to an ultrasound therapy system using high-intensity focused ultrasound. The present invention improves ultrasound and heat release characteristics and provides an ultrasound probe which easily performs manufacturing and maintenance processes. According to the present invention, a housing is recessed on the inward side around the upper-part edge. A plurality of mounting holes are uniformly formed from the outside at a constant radius to the edge in the center of the upper part. And a plurality of probe units are respectively installed to the plurality of mounting holes to form a sphere in the upper part of the housing wherein a first connection pin is protruded to the lower part of the housing in the lower part of a copper connection bar and a rear block, a piezoelectric wafer, and an acoustic matching layer are sequentially stacked on the upper part of the connection bar.

15 Claims, 5 Drawing Sheets

(56) References Cited

U.S. PATENT DOCUMENTS

| | | |
|---|---|---|
| 5,739,625 A | 4/1998 | Falcus |
| 6,599,256 B1 * | 7/2003 | Acker et al. ............... 601/2 |
| 2003/0187356 A1 | 10/2003 | Wakabayashi et al. |
| 2010/0154547 A1 * | 6/2010 | Fukada et al. ............... 73/632 |

FOREIGN PATENT DOCUMENTS

| | | |
|---|---|---|
| JP | 02580090 | 2/1997 |
| JP | 2002224104 A | 8/2002 |
| WO | 2006/021851 | 3/2006 |

* cited by examiner

ULTRASOUND PROBE

CROSS REFERENCE TO RELATED APPLICATION

This application claims the priority of Korean Patent Application No. 10-2010-0004542, filed on Jan. 18, 2010 in the KIPO (Korean Intellectual Property Office). Further, this application is the National Phase application of International Application No. PCT/KR2010/004601 filed Jul. 15, 2010, which designates the United States and was published in Korean.

TECHNICAL FIELD

The present invention relates to an ultrasound treatment system using high-intensity focused ultrasound and, more particularly, to an ultrasound probe of the ultrasound treatment system which easily performs manufacturing and maintenance processes.

BACKGROUND ART

Recently, ultrasound treatment has increased the range of use. With the growth of ultrasound treatment, a specific ultrasound treatment, especially high-intensity focused ultrasound (HIFU), is applied to damaging dose in order to effectively cure many types of disease, especially tumor. In comparison with conventional surgical operation and chemotherapy, HIFU treatment may hardly traumatize patients and also realize non-invasive treatment. Therefore, HIFU treatment is increasing in clinical applications. For example, HIFU treatment are being used for liver cancer, bone sarcoma, breast cancer, pancreas cancer, kidney cancer, soft tissue tumor, pelvic tumor, and the like.

Such an ultrasound treatment apparatus employs in general an ultrasound probe using a sphere focusing. Ultrasound emitted from all points of the ultrasound probe proceeds toward the center of a sphere, thus forming focused ultrasound. An emitter of the ultrasound treatment apparatus emits ultrasound from the outside to the inside of a body, and this forms a high-energy focused point by being focused during emission and transmission. Highly intensive and continuous ultrasound energy is applied to a target region of a treatment subject. Excessively high temperature (65~100° C.), cavitation effect, mechanical effect and acoustic-chemical effect may selectively cause coagulative necrosis of ailing organization and also prevent proliferation, invasion and metastasis of tumors.

This ultrasound treatment apparatus requires more exact, safer, and more effective localization of a focused point during HIFU treatment and also requires more convenient operability for locating the target.

DETAILED DESCRIPTION OF THE INVENTION

Technical Problems

Accordingly, an object of the present invention is to provide an ultrasound probe with improved ultrasound and heat dissipation characteristics.

Another object of the present invention is to provide an ultrasound probe which can easily perform manufacturing and maintenance processes.

Technical Solutions

In order to accomplish the above objects, the present invention provides an ultrasound probe that comprises a housing and a plurality of probe units. The housing is recessed inward from edges at an upper part thereof and has a plurality of mounting holes formed apart from a center and to the edges. The plurality of probe units are installed in the mounting holes, respectively, so that a spherical surface for a spherical focusing is formed at the upper part of the housing.

In the ultrasound probe of the present invention, each of the probe units may include a connection bar having electric and thermal conductivity, a first connection pin formed on a lower surface of the connection bar and protruded from a lower part of the housing through the mounting hole of the housing, a rear block formed on an upper surface of the connection bar and having an inclined plane for forming the spherical surface, a piezoelectric wafer formed on the inclined plane of the rear block, and a plurality of acoustic matching layers formed on an upper surface of the piezoelectric wafer.

In the ultrasound probe of the present invention, each of the probe units may further include a grounding film formed on the acoustic matching layer and forming the spherical surface.

In the ultrasound probe of the present invention, the mounting holes may be arranged in a radial form in the housing.

In the ultrasound probe of the present invention, the mounting holes may be arranged along ring-shaped coaxial regions which are disposed beyond a certain radius from the center of the spherical surface and to the edges of the spherical surface.

In the ultrasound probe of the present invention, stacks of the rear block, the piezoelectric wafer, the acoustic matching layer and the grounding film formed on the first connection pin may have a first length at a first region toward the center of the housing and a second length at a second region toward the edges of the housing, the first length being shorter than the second length.

In the ultrasound probe of the present invention, the probe units arranged along the same ring-shaped region may have the same shape.

In the ultrasound probe of the present invention, the probe units may have increasing length according as positions thereof become more distant from the center of the housing, and the first connection pins protruded from the lower part of the housing may be all the same length.

In the ultrasound probe of the present invention, the connection bars located at different ring-shaped regions may have different lengths which increase according as positions thereof become closer to the edges and become more distant from the center of the housing.

In the ultrasound probe of the present invention, the connection bar of the probe unit may have at a lower part thereof a first pin hole into which the first connection pin is inserted.

In the ultrasound probe of the present invention, the rear block may have a second connection pin extruded from a lower surface thereof, and the connection bar of the probe unit may have at an upper part thereof a second pin hole into which the second connection pin is inserted.

In the ultrasound probe of the present invention, the mounting hole may include a first mounting hole formed at the lower part of the housing such that the first connection pin is inserted into the first mounting hole and protruded from the first mounting hole, a second mounting hole vertically connected to the first mounting hole such that the connection bar is inserted into the second mounting hole, and a third mounting hole vertically connected to the second mounting hole such that the rear block is inserted into the third mounting hole.

In the ultrasound probe of the present invention, the connection bar of the probe unit may be formed of copper.

In the ultrasound probe of the present invention, the rear block of the probe unit may be formed of graphite, the piezoelectric wafer may be formed of PZT or PMN-PT, and the grounding film may be formed of polyimide film.

The ultrasound probe of the present invention may further comprise a cover layer covering the spherical surface formed by the plurality of probe units.

Advantageous Effects

Since a plurality of probe units are installed in the housing and further a spherical surface is formed at the upper part of the housing, the ultrasound probe according to the present invention may enhance ultrasound characteristics (acoustic characteristics) through the control of the plurality of probe units. Also, since the probe units are arranged along a plurality of ring-shaped coaxial regions which are disposed beyond a certain radius from the center of the spherical surface and to the edges of the spherical surface, and since each ring-shaped region has a plurality of divided sections, acoustic loss caused by empty spaces between the probe units may be prevented and thus ultrasound characteristics may be enhanced. And also, since the probe units located at adjacent ring-shaped regions are arranged differently in zigzags, ultrasound characteristics may be enhanced and further a unifying force between the probe units may be improved.

The probe unit has at the lower part thereof the connection pin and has at the upper part thereof a stack structure of the rear block, the piezoelectric wafer, the acoustic matching layer, and the grounding film via the connection bar of copper. Therefore, heat dissipation efficiency may be enhanced through the connection bar.

The ultrasound probe according to this invention is manufactured by inserting the probe unit into the mounting hole formed in the housing, so a manufacturing process is simplified. Also, since the probe unit is detachable from the housing, a maintenance process is allowed for each of the probe units. Therefore, when some parts of the ultrasound probe are defective, there is no need to replace the entire ultrasound probe and hence unnecessary cost loss may be prevented.

Since the connection pins are extruded from the lower part of the housing, the ultrasound probe according to this invention can be connected to the main body of the ultrasound treatment system using the connector cable of a connector coupling manner rather than a wiring manner. Therefore, the ultrasound treatment system has an advantage of simply performing a maintenance process for the ultrasound probe by detaching the ultrasound probe from the connector cable.

BEST MODE FOR CARRYING OUT THE INVENTION

Embodiments of the present invention will now be described more fully with reference to the accompanying drawings.

Figure 1:
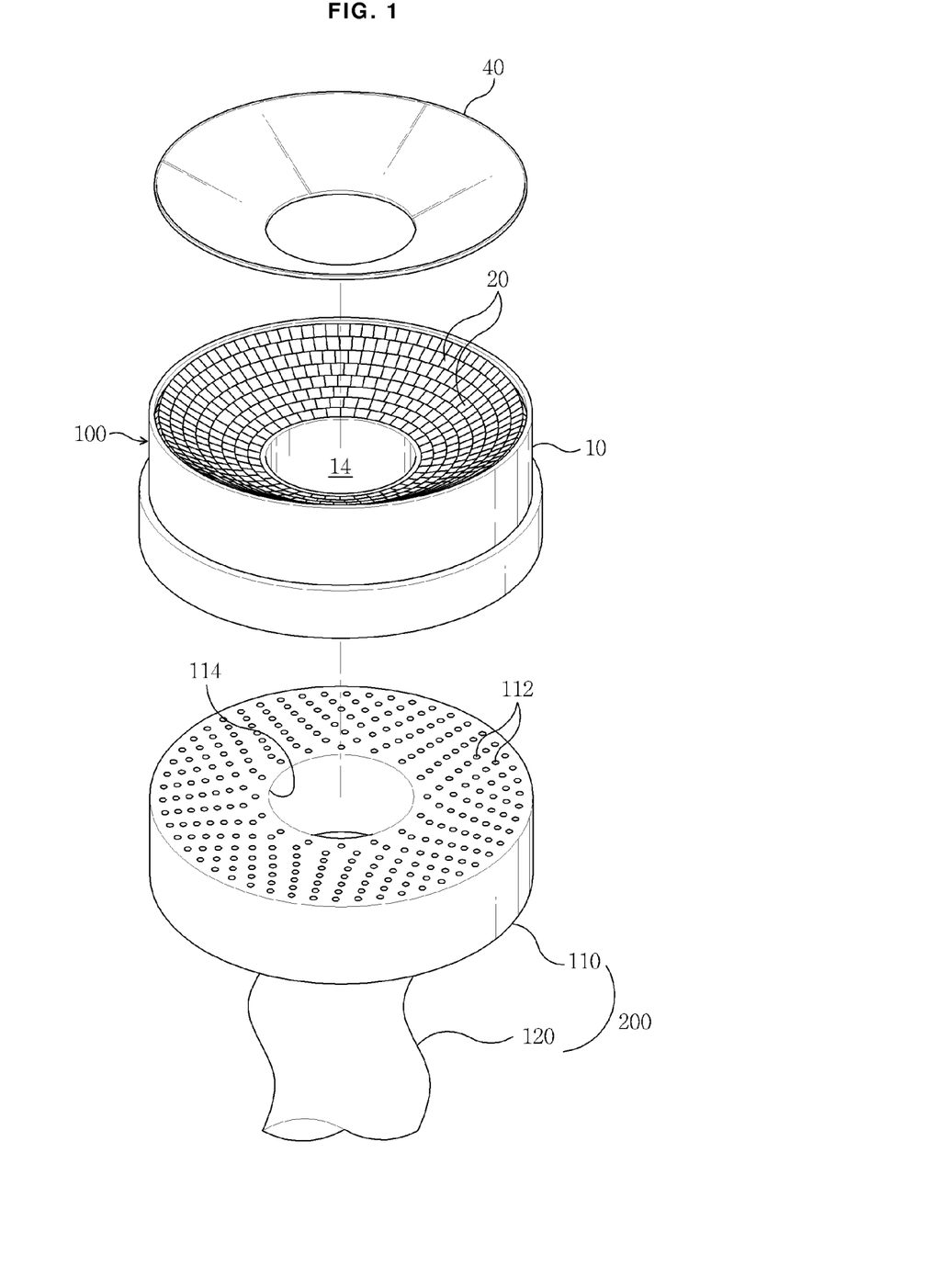
FIG. 1 is a perspective view illustrating a state in which a connector cable is connected to an ultrasound probe in accordance with an embodiment of the present invention.
Figure 2:
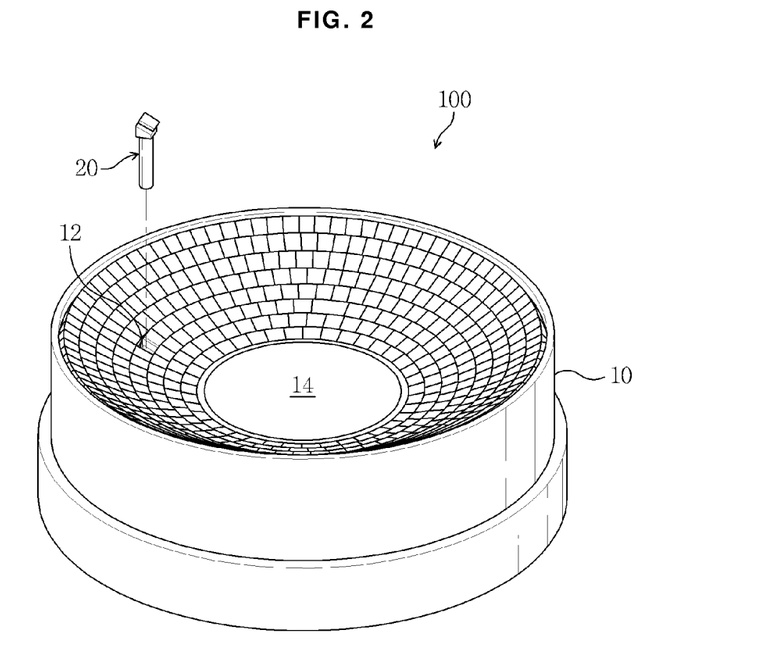
FIG. 2 is a perspective view illustrating the ultrasound probe in accordance with an embodiment of the present invention.
Figure 3:
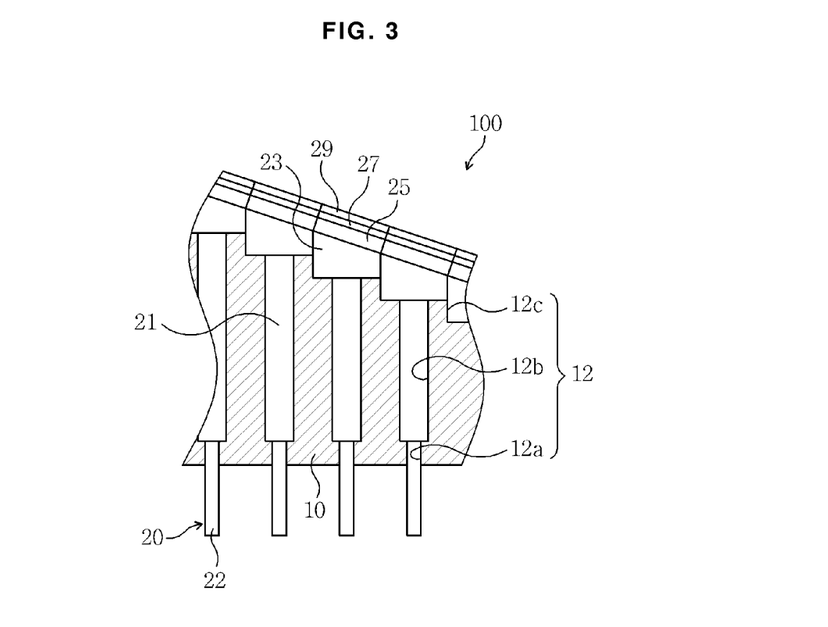
FIG. 3 is a cross-sectional view illustrating the ultrasound probe shown in FIG. 2.
Figure 4:
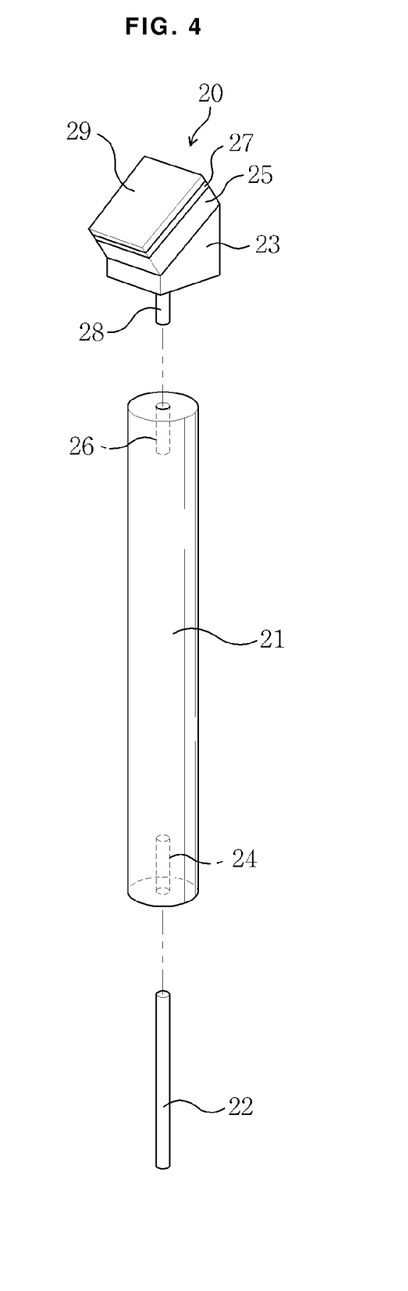
FIG. 4 is a perspective view illustrating a probe unit shown in FIG. 2.

As shown in FIGS. 1 to 3, an ultrasound probe 100 according to an embodiment of the present invention is connected to a main body of an ultrasound treatment system in a connector coupling manner using a connector cable 200.

The ultrasound probe 100 includes a housing 10, a plurality of probe units 20 installed in the housing 10 to form a spherical surface at the upper part of the housing 10, and a cover layer 40 covering the spherical surface formed by the plurality of probe units 20. Namely, the upper surface of the ultrasound probe 100 is formed with a bowl-shaped spherical surface in order to offer a spherical focusing. In the ultrasound probe 100, first connection pins 22 of the probe unit 20 are uniformly extruded from the lower surface of the housing 10. A through hole 14 is formed at the central part of the housing 10. The cover layer 40 protects the spherical surface formed by the plurality of probe units 20. Silicone material may be used for the cover layer 40.

Additionally, the connector cable 200 includes a connector 110 having connection holes 112 which correspond to the first connection pins 22, and a cable 120 which electrically couples the first connection pins 22 inserted into the connector 110 to the main body of the ultrasound treatment system. The main body of the ultrasound treatment system applies a driving signal to the ultrasound probe 100 through the connector cable 200, and in response to the driving signal the ultrasound probe 100 generates high-intensity focused ultrasound required for ultrasound treatment.

As shown, the connector 110 of the connector cable 200 has, at the central part thereof, a through hole 114 which corresponds to a through hole 14 of the housing 10. However, instead of the through hole, any hole with a limited depth may be formed or no hole may be formed.

Since the first connection pins 22 are extruded from the lower part of the housing 10, the ultrasound probe 100 according to an embodiment of this invention can be connected to the main body of the ultrasound treatment system using the connector cable 200 of a connector coupling manner rather than a wiring manner. Therefore, the ultrasound treatment system has an advantage of simply performing a maintenance process for the ultrasound probe 100 by detaching the ultrasound probe 100 from the connector cable 200.

As shown in FIGS. 1 to 6, the ultrasound probe 100 according to an embodiment of this invention includes the housing 10 and the probe unit 20 and may further include the cover layer 40. The housing 10 is recessed inward from edges at the upper part thereof, and a plurality of mounting holes 12 are formed apart from the center and to the edges. Additionally, the probe units 20 are installed in the mounting holes 12, respectively, so that a spherical surface for a spherical focusing is formed at the upper part of the housing 10.

Particularly, the housing 10 has a cylindrical shape, has the through hole 14 formed at the central part thereof, and has the spherical upper part around the central part. The housing 10 may be formed of rigid plastic material such as polyethylene (PE), polypropylene (PP), polystyrene (PS), polyethyleneterephthalate (PET), acrylonitrile-butandiene-styrene (ABS), or the like.

The mounting holes 12 are arranged in a radial form in the housing 10. Specifically, the mounting holes 12 may be arranged along ring-shaped coaxial regions which are disposed beyond a certain radius from the center of the spherical surface and to the edges of the spherical surface. Each mounting hole 12 is parallel to the central axis of the housing 10 and has the first mounting hole 12a, the second mounting hole 12b, and the third mounting hole 12c. From the first mounting hole 12a to the third mounting hole 12c, the diameter of hole is gradually increased. A related description will be described later.

The probe units 20 are inserted into the mounting holes 12 of the housing 10, respectively. In each of the probe units 20, the lower end is protruded from the lower part of the housing 10, and the upper end is protruded from the upper part of the housing 10, forming the spherical surface. The probe unit 20 has a connection bar 21, the first connection pin 22, a rear block 23, a piezoelectric wafer 25, and an acoustic matching layer 27, and may further have a grounding film 29. A second connection pin 28 is formed on the lower surface of the rear block 23.

Figure 5:
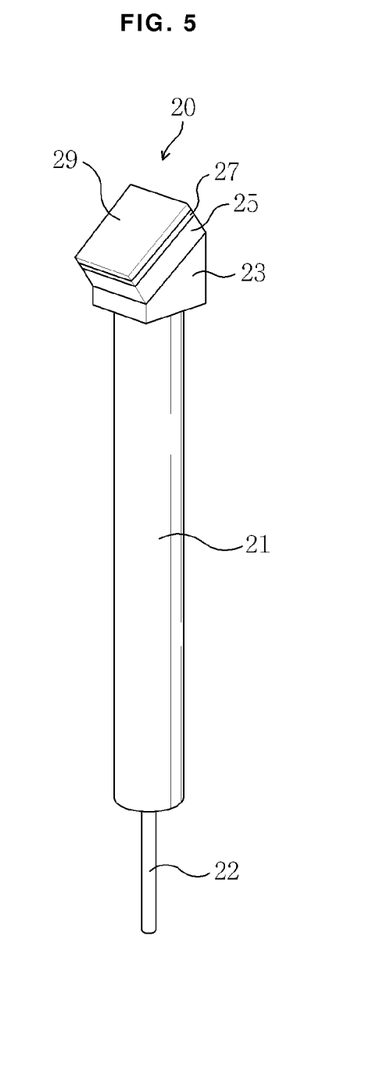
FIG. 5 is a perspective view illustrating the probe unit shown in FIG. 4.
Figure 6:
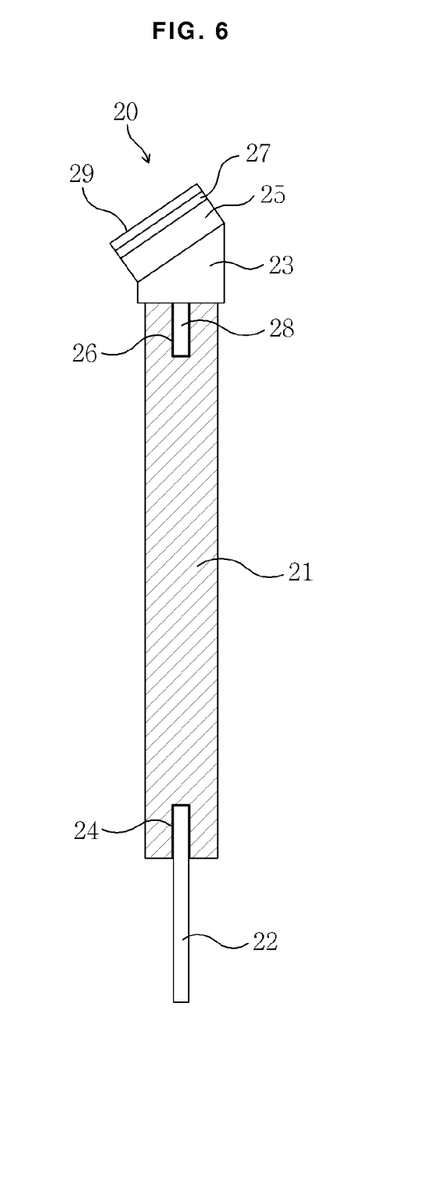
FIG. 6 is a cross-sectional view illustrating the probe unit shown in FIG. 5.

The connection bar 21 is formed of electrically and thermally conductive material and has a pole shape. Copper or any other metal having good electric and thermal conductivity may be used for the connection bar 21.

The first connection pin 22 is formed on the lower surface of the connection bar 21 and protruded from the lower part of the housing 10 through the mounting hole 12 of the housing 10. The connection bar 21 has the first pin hole 24 which is formed in the lower surface thereof and into which the first connection pin 22 is partially inserted. Alternatively, the first connection pin 22 may be integrated with the connection bar 21.

The rear block 23 is formed on the upper surface of the connection bar 21, and the upper part of the rear block 23 forms an inclined plane so as to ultimately form the spherical surface. The rear block 23 absorbs unnecessary ultrasound signals which travel from the piezoelectric wafer 25 to the rear block 23. The rear block 23 may be formed of rubber or graphite which has a good sound absorption property. As shown in FIG. 6, the rear block 23 has a form partially removed from a rectangular parallelepiped and thus has a cross section of trapezoid form. A removed surface forms the inclined plane of the rear block 23.

The second connection pin 28 integrated with the rear block 23 is extruded from the lower surface of the rear block 23. The second pin hole 26 is formed in the upper surface of the connection bar 21, so that the second connection pin 28 can be inserted into the second pin hole 26. Therefore, the rear block 23 is joined to the connection bar 21 via the second connection pin 28 inserted into the second pin hole 26. The lower surface of the rear block 23 adheres closely to the upper surface of the connection bar 21.

The first and second connection pins 22 and 28 may be fixedly inserted into the first and second pin holes 24 and 26 in a forced insertion manner or using electrically conductive adhesive.

The piezoelectric wafer 25, the acoustic matching layer 27 and the grounding film 29 are sequentially formed on the inclined plane of the rear block 23 so as to be parallel to the inclined plane. Namely, each of the piezoelectric wafer 25, the acoustic matching layer 27 and the grounding film 29 has a rectangular parallelepiped form having upper and lower surfaces corresponding to the inclined plane of the rear block 23 and is sequentially stacked. Therefore, in an embodiment, a stack of the piezoelectric wafer 25, the acoustic matching layer 27 and the grounding film 29 is laterally protruded from the lower end of the inclined plane as shown. Alternatively, the stack may be formed so as not to exceed the lateral surface of the rear block 23. In this case, each of the piezoelectric wafer 25, the acoustic matching layer 27 and the grounding film 29 has upper and lower surfaces corresponding to the inclined plane of the rear block 23 and has a cross section of trapezoid form.

The piezoelectric wafer 25 is formed on the inclined plane of the rear block 23 and generates ultrasound. The piezoelectric wafer 25 is divided into a plurality of devices in a scan direction. Ceramic material such as PZT or PMN-PT may be used for the piezoelectric wafer 25.

The acoustic matching layer 27 is formed on the upper surface of the piezoelectric wafer 25 and performs an acoustic matching function for the ultrasound generated from the piezoelectric wafer 25. The acoustic matching layer 27 may be composed of at least one layer. Also, the acoustic matching layer 27 may be formed of metal powder, ceramic powder, silicon wafer, and the like.

The grounding film 29 is formed on the acoustic matching layer 27 and forms a spherical surface. A polyimide film may be used for the grounding film 29.

Particularly, the probe unit 20 is installed in each mounting hole 12 of the housing 10, and the probe units 20 arranged along the same ring-shaped region have the same shape. The mounting holes 12 have increasing length according as their positions become more distant from the center of the housing 10. The probe units 20 have also increasing length as shown in FIG. 3, but the first connection pins 22 protruded from the lower part of the housing 10 are all the same length. In the probe units 20, the connection bars 21 located at different ring-shaped regions have different lengths which increase according as their positions become closer to the edges, namely, become more distant from the center of the housing 10.

As discussed above and shown in FIG. 3, the mounting hole 12 of the housing 10 into which the probe unit 20 is fixedly installed includes the first to third mounting holes 12a, 12b and 12c. The first mounting hole 12a is formed at the lower part of the housing 10, and the first connection pin 22 is inserted thereinto and protruded therefrom. The second mounting hole 12b is vertically connected to the first mounting hole 12a, and the connection bar 21 is inserted thereinto. The lower surface of the connection bar 21 is mounted on the bottom of the second mounting hole 12b communicating with the first mounting hole 12a. The third mounting hole 12c is vertically connected to the second mounting hole 12b, and the rear block 23 is inserted thereinto. The third mounting hole 12c accommodates a part of the rear block 23 of the probe unit 20, so that the piezoelectric wafer 25, the acoustic matching layer 27 and the grounding film 29 stacked on the rear block 23 are located out of the third mounting hole 12c.

In order that the probe unit 20 can be stably inserted and fixed, the mounting hole 12 of the housing 10 is formed to be adapted for the shape of the probe unit 20. For example, if each of the first connection pin 22 and the connection bar 21 of the probe unit 20 has a circular cross section in a plan view, each of the first and second mounting holes 12a and 12b is formed to have a circular cross section in a plan view. Also, if the rear block 23 has a rectangular cross section in a plan view, the third mounting hole 12c is formed to have a rectangular cross section in a plan view.

The probe unit 20 may be fixedly inserted into the mounting hole 12 of the housing 10 through adhesive or in a forced insertion manner. Also, the probe unit 20 may be installed in the mounting hole 12 of the housing 10 in a screw coupling manner. And also, any other well known manners may be used for installing the probe unit 20 into the mounting hole 12 of the housing 10.

As discussed above, since a plurality of probe units 20 are installed in the housing 10 and further a spherical surface is formed at the upper part of the housing 10, the ultrasound probe 100 according to an embodiment may enhance ultrasound characteristics (acoustic characteristics) through the control of the plurality of probe units 20. Also, since the probe units 20 are arranged along a plurality of ring-shaped coaxial regions which are disposed beyond a certain radius from the center of the spherical surface and to the edges of the spherical surface, and since each ring-shaped region has a plurality of divided sections, acoustic loss caused by empty spaces between the probe units 20 may be prevented and thus ultrasound characteristics may be enhanced. And also, since the probe units 20 located at adjacent ring-shaped regions are arranged differently in zigzags, ultrasound characteristics may be enhanced and further a unifying force between the probe units 20 may be improved.

The probe unit 20 of the ultrasound probe 100 according to an embodiment has at the lower part thereof the first connection pin 22 and has at the upper part thereof a stack structure of the rear block 23, the piezoelectric wafer 25, the acoustic matching layer 27, and the grounding film 29 via the connection bar 22 of copper. Therefore, heat dissipation efficiency may be enhanced through the connection bar 22.

The ultrasound probe 100 according to an embodiment is manufactured by inserting the probe unit 20 into the mounting hole 12 formed in the housing 10, so a manufacturing process is simplified. Also, since the probe unit 20 is detachable from the housing 10, a maintenance process is allowed for each of the probe units 20. Therefore, when some parts of the ultrasound probe 100 are defective, there is no need to replace the entire ultrasound probe 100 and hence unnecessary cost loss may be prevented.

Now, a method for manufacturing the ultrasound probe 100 according to an embodiment will be described. At the outset, the housing 10 and the plurality of probe units 20 to be inserted into the mounting holes 12 of the housing 10 are prepared.

Next, the probe units 20 are inserted into the mounting holes 12 located near the through hole 14 of the housing 10 and fixedly installed through adhesive. At this time, the inserted probe units 20 form a ring shape. Then, in the same manner, other probe units 20 are inserted and fixedly installed in the next mounting holes 12 which are outwardly adjacent to the previously inserted probe units 20. In this manner, the probe units 20 are inserted and fixedly installed in all the mounting holes 12 of the housing 10 sequentially from the near side of the through hole 14 to the far side.

Also, the cover layer 40 is covered on a spherical surface formed by the plurality of probe units 20, and thus a manufacturing process of the ultrasound probe 100 is completed. The cover layer 40 may be formed in an adhering or coating manner to cover the spherical surface.

In the above-discussed manufacturing process, the reason the probe units 20 are installed from the inner side of the housing 10 is that a stack of the piezoelectric wafer 25, the acoustic matching layer 27 and the grounding film 29 is laterally protruded from the lower end of the inclined plane of the rear block 23.

Alternatively, if used is the probe unit having the stack of the piezoelectric wafer, the acoustic matching layer and the grounding film without exceeding the lateral surface of the rear block, there is no need to install the probe units in a sequential manner discussed above. Namely, since the probe unit has the stack which is not protruded from the lateral surface of the rear block, the probe units may be inserted and installed in the housing regardless of the order if only the same probe units are arranged in the same ring-shaped region.

While this invention has been particularly shown and described with reference to an exemplary embodiment thereof, it will be understood by those skilled in the art that various changes in form and details may be made therein without departing from the spirit and scope of the invention as defined by the appended claims.

What is claimed is:

1. An ultrasound probe, comprising:
   a housing recessed inward from edges at an upper part thereof and having a plurality of mounting holes formed apart from a center and to the edges; and
   a plurality of probe units installed in the mounting holes, respectively, so that a spherical surface for a spherical focusing is formed at the upper part of the housing,
   wherein each of the probe units includes:
      a connection bar having electric and thermal conductivity;
      a first connection pin formed on a lower surface of the connection bar and protruded from a lower part of the housing through the corresponding mounting hole of the housing;
      a rear block formed on an upper surface of the connection bar and having an inclined plane for forming the spherical surface;
      a piezoelectric wafer formed on the inclined plane of the rear block; and
      at least one acoustic matching layer formed on an upper surface of the piezoelectric wafer.

2. The ultrasound probe of claim 1, wherein each of the probe units further includes:
   a grounding film formed on the acoustic matching layer and forming the spherical surface.

3. The ultrasound probe of claim 2, wherein the mounting holes are arranged in a radial form in the housing.

4. The ultrasound probe of claim 3, wherein a stack of the rear block, the piezoelectric wafer, the acoustic matching layer and the grounding film formed on the first connection pin has a first length at a first region toward the center of the housing and a second length at a second region toward the edges of the housing, the first length being shorter than the second length.

5. The ultrasound probe of claim 2, wherein the mounting holes are arranged along ring-shaped coaxial regions which are disposed beyond a certain radius from the center of the spherical surface and to the edges of the spherical surface.

6. The ultrasound probe of claim 5, wherein the probe units arranged along the same ring-shaped region have the same shape.

7. The ultrasound probe of claim 6, wherein the probe units have increasing lengths as positions thereof become more distant from the center of the housing, and wherein the first connection pins protruded from the lower part of the housing are all of the same length.

8. The ultrasound probe of claim 7, wherein the connection bars located at different ring-shaped regions have different lengths which increase as positions thereof become closer to the edges of the housing and become more distant from the center of the housing.

9. The ultrasound probe of claim 2, wherein a stack of the rear block, the piezoelectric wafer, the acoustic matching layer and the grounding film formed on the first connection pin has a first length at a first region toward the center of the housing and a second length at a second region toward the edges of the housing, the first length being shorter than the second length.

10. The ultrasound probe of claim 2, wherein the connection bar of the probe unit has at a lower part thereof a first pin hole into which the first connection pin is inserted.

11. The ultrasound probe of claim 10, wherein the rear block has a second connection pin extruded from a lower surface thereof, and wherein the connection bar of the probe unit has at an upper part thereof a second pin hole into which the second connection pin is inserted.

12. The ultrasound probe of claim 11, wherein the mounting hole includes:
- a first mounting hole section formed at the lower part of the housing such that the first connection pin is inserted into the first mounting hole section and protruded from the first mounting hole section;
- a second mounting hole section vertically connected to the first mounting hole section such that the connection bar is inserted into the second mounting hole section; and
- a third mounting hole section vertically connected to the second mounting hole section such that the rear block is inserted into the third mounting hole section.

13. The ultrasound probe of claim 2, wherein the connection bar of the probe unit is formed of copper.

14. The ultrasound probe of claim 2, wherein the rear block of the probe unit is formed of graphite, wherein the piezoelectric wafer is formed of PZT or PMN-PT, and wherein the grounding film is formed of a polyimide film.

15. The ultrasound probe of claim 1, further comprising:
- a cover layer covering the spherical surface formed by the plurality of probe units.

* * * * *